US007387810B2

(12) United States Patent
Hossainy

(10) Patent No.: US 7,387,810 B2
(45) Date of Patent: Jun. 17, 2008

(54) METHOD OF FORMING RATE LIMITING BARRIERS FOR IMPLANTABLE DEVICES

(75) Inventor: Syed F. A. Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 272 days.

(21) Appl. No.: 11/053,184

(22) Filed: Feb. 7, 2005

(65) Prior Publication Data

US 2005/0191332 A1 Sep. 1, 2005

Related U.S. Application Data

(62) Division of application No. 10/293,064, filed on Nov. 12, 2002, now Pat. No. 6,896,965.

(51) Int. Cl.
B05D 3/02 (2006.01)
B05D 3/06 (2006.01)

(52) U.S. Cl. .............. 427/2.1; 427/2.24; 427/2.25; 427/508; 427/517; 427/519; 427/407.1

(58) Field of Classification Search ............ 427/2.11, 427/2.12, 301, 387, 407, 512; 428/216, 336, 428/448, 451
See application file for complete search history.

(56) References Cited

U.S. PATENT DOCUMENTS

| | | | |
|---|---|---|---|
| 2,072,303 A | 3/1937 | Herrmann et al. |
| 2,386,454 A | 10/1945 | Frosch et al. |
| 3,773,737 A | 11/1973 | Goodman et al. |
| 3,849,514 A | 11/1974 | Gray, Jr. et al. |
| 4,226,243 A | 10/1980 | Shalaby et al. |
| 4,329,383 A | 5/1982 | Joh |
| 4,343,931 A | 8/1982 | Barrows |
| 4,529,792 A | 7/1985 | Barrows |
| 4,611,051 A | 9/1986 | Hayes et al. |
| 4,656,242 A | 4/1987 | Swan et al. |
| 4,678,468 A | 7/1987 | Hiroyoshi |
| 4,733,665 A | 3/1988 | Palmaz |
| 4,800,882 A | 1/1989 | Gianturco |
| 4,816,339 A | 3/1989 | Tu et al. |
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,100,992 A | 3/1992 | Cohn et al. |
| 5,112,457 A | 5/1992 | Marchant |
| 5,133,742 A | 7/1992 | Pinchuk |
| 5,163,952 A | 11/1992 | Froix |
| 5,165,919 A | 11/1992 | Sasaki et al. |
| 5,219,980 A | 6/1993 | Swidler |
| 5,258,020 A | 11/1993 | Froix |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,380,299 A | 1/1995 | Fearnot et al. |
| 5,417,981 A | 5/1995 | Endo et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,485,496 A | 1/1996 | Lee et al. |
| 5,516,881 A | 5/1996 | Lee et al. |
| 5,569,463 A | 10/1996 | Helmus et al. |
| 5,578,073 A | 11/1996 | Haimovich et al. |
| 5,584,877 A | 12/1996 | Miyake et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |

(Continued)

FOREIGN PATENT DOCUMENTS

DE 42 24 401 1/1994

(Continued)

OTHER PUBLICATIONS

Anonymous, *Cardiologists Draw—Up The Dream Stent*, Clinica 710:15 (Jun. 17, 1996), http://www.dialogweb.com/cgi/document?reg=1061848202959, printed Aug. 25, 2003 (2 pages).

Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

(Continued)

*Primary Examiner*—Erma Cameron
(74) *Attorney, Agent, or Firm*—Squire Sanders & Dempsey, LLP

(57) ABSTRACT

A method is disclosed for forming a coating on implantable medical devices including an interpenetrating polymer network that serves as a rate limiting barrier.

15 Claims, No Drawings

U.S. PATENT DOCUMENTS

| | | | |
|---|---|---|---|
| 5,649,977 | A | 7/1997 | Campbell |
| 5,658,995 | A | 8/1997 | Kohn et al. |
| 5,667,767 | A | 9/1997 | Greff et al. |
| 5,670,558 | A | 9/1997 | Onishi et al. |
| 5,674,242 | A | 10/1997 | Phan et al. |
| 5,679,400 | A | 10/1997 | Tuch |
| 5,700,286 | A | 12/1997 | Tartaglia et al. |
| 5,702,754 | A | 12/1997 | Zhong |
| 5,711,958 | A | 1/1998 | Cohn et al. |
| 5,716,981 | A | 2/1998 | Hunter et al. |
| 5,721,131 | A | 2/1998 | Rudolph et al. |
| 5,723,219 | A | 3/1998 | Kolluri et al. |
| 5,735,897 | A | 4/1998 | Buirge |
| 5,746,998 | A | 5/1998 | Torchilin et al. |
| 5,759,205 | A | 6/1998 | Valentini |
| 5,776,184 | A | 7/1998 | Tuch |
| 5,783,657 | A | 7/1998 | Pavlin et al. |
| 5,788,979 | A | 8/1998 | Alt et al. |
| 5,800,392 | A | 9/1998 | Racchini |
| 5,820,917 | A | 10/1998 | Tuch |
| 5,824,048 | A | 10/1998 | Tuch |
| 5,824,049 | A | 10/1998 | Ragheb et al. |
| 5,830,178 | A | 11/1998 | Jones et al. |
| 5,837,008 | A | 11/1998 | Berg et al. |
| 5,837,313 | A | 11/1998 | Ding et al. |
| 5,849,859 | A | 12/1998 | Acemoglu |
| 5,851,508 | A | 12/1998 | Greff et al. |
| 5,854,376 | A | 12/1998 | Higashi |
| 5,857,998 | A | 1/1999 | Barry |
| 5,858,746 | A | 1/1999 | Hubbell et al. |
| 5,863,650 | A * | 1/1999 | Healy et al. ............ 428/336 |
| 5,865,814 | A | 2/1999 | Tuch |
| 5,869,127 | A | 2/1999 | Zhong |
| 5,873,904 | A | 2/1999 | Ragheb et al. |
| 5,876,433 | A | 3/1999 | Lunn |
| 5,877,224 | A | 3/1999 | Brocchini et al. |
| 5,879,713 | A | 3/1999 | Roth et al. |
| 5,902,875 | A | 5/1999 | Roby et al. |
| 5,905,168 | A | 5/1999 | Dos Santos et al. |
| 5,910,564 | A | 6/1999 | Gruning et al. |
| 5,914,387 | A | 6/1999 | Roby et al. |
| 5,919,893 | A | 7/1999 | Roby et al. |
| 5,925,720 | A | 7/1999 | Kataoka et al. |
| 5,932,299 | A | 8/1999 | Katoot |
| 5,955,509 | A | 9/1999 | Webber et al. |
| 5,958,385 | A | 9/1999 | Tondeur et al. |
| 5,962,007 | A | 10/1999 | Cooper et al. |
| 5,962,138 | A | 10/1999 | Kolluri et al. |
| 5,971,954 | A | 10/1999 | Conway et al. |
| 5,980,928 | A | 11/1999 | Terry |
| 5,980,972 | A | 11/1999 | Ding |
| 5,997,517 | A | 12/1999 | Whitbourne |
| 6,010,530 | A | 1/2000 | Goicoechea |
| 6,011,125 | A | 1/2000 | Lohmeijer et al. |
| 6,015,541 | A | 1/2000 | Greff et al. |
| 6,033,582 | A | 3/2000 | Lee et al. |
| 6,034,204 | A | 3/2000 | Mohr et al. |
| 6,042,875 | A | 3/2000 | Ding et al. |
| 6,051,576 | A | 4/2000 | Ashton et al. |
| 6,051,648 | A | 4/2000 | Rhee et al. |
| 6,054,553 | A | 4/2000 | Groth et al. |
| 6,056,993 | A | 5/2000 | Leidner et al. |
| 6,060,451 | A | 5/2000 | DiMaio et al. |
| 6,060,518 | A | 5/2000 | Kabanov et al. |
| 6,080,488 | A | 6/2000 | Hostettler et al. |
| 6,096,070 | A | 8/2000 | Ragheb et al. |
| 6,099,562 | A | 8/2000 | Ding et al. |
| 6,110,188 | A | 8/2000 | Narciso, Jr. |
| 6,110,483 | A | 8/2000 | Whitbourne et al. |
| 6,113,629 | A | 9/2000 | Ken |
| 6,120,491 | A | 9/2000 | Kohn et al. |
| 6,120,536 | A | 9/2000 | Ding et al. |
| 6,120,788 | A | 9/2000 | Barrows |
| 6,120,904 | A | 9/2000 | Hostettler et al. |
| 6,121,027 | A | 9/2000 | Clapper et al. |
| 6,129,761 | A | 10/2000 | Hubbell |
| 6,136,333 | A | 10/2000 | Cohn et al. |
| 6,143,354 | A | 11/2000 | Koulik et al. |
| 6,153,252 | A | 11/2000 | Hossainy et al. |
| 6,159,978 | A | 12/2000 | Myers et al. |
| 6,165,212 | A | 12/2000 | Dereume et al. |
| 6,172,167 | B1 | 1/2001 | Stapert et al. |
| 6,177,523 | B1 | 1/2001 | Reich et al. |
| 6,180,632 | B1 | 1/2001 | Myers et al. |
| 6,203,551 | B1 | 3/2001 | Wu |
| 6,211,249 | B1 | 4/2001 | Cohn et al. |
| 6,214,901 | B1 | 4/2001 | Chudzik et al. |
| 6,231,600 | B1 | 5/2001 | Zhong |
| 6,240,616 | B1 | 6/2001 | Yan |
| 6,245,753 | B1 | 6/2001 | Byun et al. |
| 6,245,760 | B1 | 6/2001 | He et al. |
| 6,248,129 | B1 | 6/2001 | Froix |
| 6,251,136 | B1 | 6/2001 | Guruwaiya et al. |
| 6,254,632 | B1 | 7/2001 | Wu et al. |
| 6,254,634 | B1 * | 7/2001 | Anderson et al. .......... 623/1.42 |
| 6,258,121 | B1 | 7/2001 | Yang et al. |
| 6,258,371 | B1 | 7/2001 | Koulik et al. |
| 6,262,034 | B1 | 7/2001 | Mathiowitz et al. |
| 6,270,788 | B1 | 8/2001 | Koulik et al. |
| 6,277,449 | B1 | 8/2001 | Kolluri et al. |
| 6,283,947 | B1 | 9/2001 | Mirzaee |
| 6,283,949 | B1 | 9/2001 | Roorda |
| 6,284,305 | B1 | 9/2001 | Ding et al. |
| 6,287,628 | B1 | 9/2001 | Hossainy et al. |
| 6,299,604 | B1 | 10/2001 | Ragheb et al. |
| 6,306,176 | B1 | 10/2001 | Whitbourne |
| 6,331,313 | B1 | 12/2001 | Wong et al. |
| 6,335,029 | B1 | 1/2002 | Kamath et al. |
| 6,344,035 | B1 | 2/2002 | Chudzik et al. |
| 6,346,110 | B2 | 2/2002 | Wu |
| 6,358,556 | B1 | 3/2002 | Ding et al. |
| 6,379,381 | B1 | 4/2002 | Hossainy et al. |
| 6,387,379 | B1 | 5/2002 | Goldberg et al. |
| 6,395,326 | B1 | 5/2002 | Castro et al. |
| 6,419,692 | B1 | 7/2002 | Yang et al. |
| 6,451,373 | B1 | 9/2002 | Hossainy et al. |
| 6,482,834 | B2 | 11/2002 | Spada et al. |
| 6,494,862 | B1 | 12/2002 | Ray et al. |
| 6,503,538 | B1 | 1/2003 | Chu et al. |
| 6,503,556 | B2 | 1/2003 | Harish et al. |
| 6,503,954 | B1 | 1/2003 | Bhat et al. |
| 6,506,437 | B1 | 1/2003 | Harish et al. |
| 6,524,347 | B1 | 2/2003 | Myers et al. |
| 6,527,801 | B1 | 3/2003 | Dutta |
| 6,527,863 | B1 | 3/2003 | Pacetti et al. |
| 6,528,526 | B1 | 3/2003 | Myers et al. |
| 6,530,950 | B1 | 3/2003 | Alvarado et al. |
| 6,530,951 | B1 | 3/2003 | Bates et al. |
| 6,540,776 | B2 | 4/2003 | Sanders Millare et al. |
| 6,544,223 | B1 | 4/2003 | Kokish |
| 6,544,543 | B1 | 4/2003 | Mandrusov et al. |
| 6,544,582 | B1 | 4/2003 | Yoe |
| 6,555,157 | B1 | 4/2003 | Hossainy |
| 6,558,733 | B1 | 5/2003 | Hossainy et al. |
| 6,565,659 | B1 | 5/2003 | Pacetti et al. |
| 6,572,644 | B1 | 6/2003 | Moein |
| 6,585,755 | B2 | 7/2003 | Jackson et al. |
| 6,585,765 | B1 | 7/2003 | Hossainy et al. |
| 6,585,926 | B1 | 7/2003 | Mirzaee |
| 6,605,154 | B1 | 8/2003 | Villareal |
| 6,616,765 | B1 | 9/2003 | Hossainy |
| 6,623,448 | B2 | 9/2003 | Slater |
| 6,625,486 | B2 | 9/2003 | Lundkvist et al. |
| 6,645,135 | B1 | 11/2003 | Bhat |

| | | |
|---|---|---|
| 6,645,195 B1 | 11/2003 | Bhat et al. |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,673,154 B1 | 1/2004 | Pacetti et al. |
| 6,673,385 B1 | 1/2004 | Ding et al. |
| 6,689,099 B2 | 2/2004 | Mirzaee |
| 6,695,920 B1 | 2/2004 | Pacetti et al. |
| 6,706,013 B1 | 3/2004 | Bhat et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,723,120 B2 | 4/2004 | Yan |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,749,626 B1 | 6/2004 | Bhat et al. |
| 6,753,071 B1 | 6/2004 | Pacetti |
| 6,758,859 B1 | 7/2004 | Dang et al. |
| 6,759,054 B2 | 7/2004 | Chen et al. |
| 6,764,505 B1 | 7/2004 | Hossainy et al. |
| 6,861,088 B2 | 3/2005 | Weber et al. |
| 6,865,810 B2 | 3/2005 | Stinson |
| 6,869,443 B2 | 3/2005 | Buscemi et al. |
| 6,878,160 B2 | 4/2005 | Gilligan et al. |
| 6,887,270 B2 | 5/2005 | Miller et al. |
| 6,887,485 B2 | 5/2005 | Fitzhugh et al. |
| 6,890,546 B2 | 5/2005 | Mollison et al. |
| 6,899,731 B2 | 5/2005 | Li et al. |
| 6,994,867 B1 * | 2/2006 | Hossainy et al. ............ 424/423 |
| 2001/0007083 A1 | 7/2001 | Roorda |
| 2001/0014717 A1 | 8/2001 | Hossainy et al. |
| 2001/0018469 A1 | 8/2001 | Chen et al. |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0094440 A1 | 7/2002 | Llanos et al. |
| 2002/0111590 A1 | 8/2002 | Davila et al. |
| 2002/0120326 A1 | 8/2002 | Michal |
| 2002/0123801 A1 | 9/2002 | Pacetti et al. |
| 2002/0142039 A1 | 10/2002 | Claude |
| 2002/0155212 A1 | 10/2002 | Hossainy |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2005/0037052 A1 | 2/2005 | Udipi et al. |
| 2005/0038134 A1 | 2/2005 | Loomis et al. |
| 2005/0038497 A1 | 2/2005 | Neuendorf et al. |
| 2005/0043786 A1 | 2/2005 | Chu et al. |
| 2005/0049693 A1 | 3/2005 | Walker |
| 2005/0049694 A1 | 3/2005 | Neary |
| 2005/0054774 A1 | 3/2005 | Kangas |
| 2005/0055044 A1 | 3/2005 | Kangas |
| 2005/0055078 A1 | 3/2005 | Campbell |
| 2005/0060020 A1 | 3/2005 | Jenson |
| 2005/0064088 A1 | 3/2005 | Fredrickson |
| 2005/0065501 A1 | 3/2005 | Wallace |
| 2005/0065545 A1 | 3/2005 | Wallace |
| 2005/0065593 A1 | 3/2005 | Chu et al. |
| 2005/0074406 A1 | 4/2005 | Couvillon, Jr. et al. |
| 2005/0074545 A1 | 4/2005 | Thomas |
| 2005/0075714 A1 | 4/2005 | Cheng et al. |
| 2005/0079274 A1 | 4/2005 | Palasis et al. |
| 2005/0084515 A1 | 4/2005 | Udipi et al. |
| 2005/0106210 A1 | 5/2005 | Ding et al. |
| 2005/0113903 A1 | 5/2005 | Rosenthal et al. |
| 2006/0073183 A1 * | 4/2006 | Ding ........................ 424/426 |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 850 651 | 7/1998 |
| EP | 0 879 595 | 11/1998 |
| EP | 0 910 584 | 4/1999 |

| | | |
|---|---|---|
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 97/45105 | 12/1947 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/46590 | 12/1997 |
| WO | WO 98/08463 | 3/1998 |
| WO | 0 832 655 | 4/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 04/000383 | 12/2003 |
| WO | WO 2004/009145 | 1/2004 |

OTHER PUBLICATIONS

Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, EPO Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

Shigeno, *Prevention of Cerebrovascular Spasm By Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

* cited by examiner

METHOD OF FORMING RATE LIMITING BARRIERS FOR IMPLANTABLE DEVICES

CROSS REFERENCE

This is a divisional application of U.S. Ser. No. 10/293,064 now U.S. Pat. No. 6,896,965, which was filed on Nov. 12, 2002, and claims the priority benefit of that application.

BACKGROUND OF THE INVENTION

1. Field of the Invention

This invention relates to coatings for controlling the rate of release of drugs from implantable medical devices such as stents.

2. Description of Related Art

In the field of medical technology, there is frequently a necessity to administer drugs locally. To provide an efficacious concentration to the treatment site, systemic administration of medication can produce adverse or toxic side effect for the patient. Local delivery is a preferred method of treatment in that smaller total levels of medication are administered in comparison to systemic dosages, but are concentrated at a specific site.

In the treatment of vascular disorders, such as arteriosclerosis, intracoronary stents are now a standard adjunct to balloon angioplasty. Stenting eliminates vasospasm, tacks dissections to the vessel wall, and reduces negative remodeling. Stents can be made from interconnected struts that are usually between 50 and 150 microns wide. Being made of a metal (for instance, stainless steel), bare stents have to be modified so as to provide a means for local drug delivery. Accordingly, stents are being modified by forming a polymer coating, containing a drug, on the surface of the stent.

A coating used to achieve local drug delivery via stent can include a three-layer structure. The three layer structure includes a drug-polymer layer serving as a reservoir for the drug, an optional primer polymer layer for improving adhesion of the drug-polymer layer to the surface of the stent, and an optional topcoat polymer layer for reducing the rate of release of the drug. The medicine to be administered will have a sustained release profile from drug-polymer layer through the topcoat polymer layer.

To the extent that the mechanical functionality of stents has been optimized in recent years, it has been determined that continued improvements could be done by means of pharmacological therapies. For the purposes of pharmacological therapy, it is important to maintain the concentration of the drug at a therapeutically effective level for an acceptable period of time. Hence, controlling a rate of release of the drug from the stent is important, especially in such a way so as to decrease the release rate of the drug from the matrix. In view of the foregoing, coatings for reducing the rate of release a therapeutic substance from implantable devices, such as stents, are desired. The coatings should prolong the residence time of the drug in the patient, among other useful functions.

SUMMARY

According to one embodiment of the present invention, a multi-layer coating for an implantable medical device is provided, wherein the outermost layer of the coating includes an interpenetrating polymer network. The interpenetrating polymer network can be formed from a product selected from a group consisting of poly(ethylene glycol)-acrylate, poly(ethylene glycol)-methacrylate, poly(ethylene glycol)-diacrylate, poly(ethylene glycol)-dimethacrylate, N-vinylpyrrolidone, heparin, and heparin derivatives, hyaluronic acid, derivatives of hyaluronic acid, poly(butyleneterephthalate-co ethylene glycol) (PBT-PEG), and mixtures thereof.

According to another embodiment of the present invention, a method for fabricating a coating on an implantable medical device is provided, the method comprises forming a polymer layer on the device, applying on the polymer layer a precursor of an interpenetrating polymer network, subjecting the device to a treatment to cause the precursor to form the interpenetrating polymer network on the device.

DETAILED DESCRIPTION

A coating for an implantable medical device, such as a stent, can include an optional primer layer, a drug-polymer layer, a topcoat layer, and an optional finishing coat layer. The drug-polymer layer can be applied directly onto the stent to serve as a reservoir for the sustained release of a therapeutic agent. The topcoat layer can serve as a rate limiting membrane which controls the rate of release of the drug. The optional primer layer can be applied between the stent and the drug-polymer layer to improve the adhesion of the coating to the stent. The finishing coat layer can be applied over the topcoat layer and can be used for improving the biocompatibility of the underlying layer.

The process of the release of the drug from a coating having both topcoat and finishing coat layers includes at least three distinctive steps. First, the drug is absorbed by the polymer of the topcoat layer on the drug-polymer layer/topcoat layer interface. Next, the drug diffuses through the topcoat layer using empty spaces between the macromolecules of the topcoat layer polymer as pathways for migration. Next, the drug arrives to the topcoat layer/finishing layer interface. Finally, the drug diffuses through the finishing coat layer in a similar fashion, arrives to the outer surface of the finishing coat layer, and desorbs from the outer surface. At this point, the drug is released into the blood stream. Consequently, a combination of the topcoat and finishing coat layers, if used, can serve as a rate limiting barrier.

The total amount of the drug in the coating can be between about 0.02 and 2.0% by mass, for example, between 0.7 and 1.2%. The drug can include any substance capable of exerting a therapeutic or prophylactic effect for a patient. The drug may include small molecule drugs, peptides, proteins, oligonucleotides, and the like. The drug could be designed, for example, to inhibit the activity of vascular smooth muscle cells. It can be directed at inhibiting abnormal or inappropriate migration and/or proliferation of smooth muscle cells to inhibit restenosis.

Examples of drugs include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin.

Poly(ethylene-co-vinyl alcohol) (EVAL) is one example of a polymer that can be included in the drug-polymer layer, the optional primer layer, the topcoat layer and the finishing coat layer. EVAL has the general formula —[$CH_2$—$CH_2$]$_m$—[$CH_2$—CH(OH)]$_n$—. EVAL is a product of hydrolysis of ethylene-vinyl acetate copolymers and may also be a terpolymer including up to 5 molar % of units derived from styrene, propylene and other suitable unsaturated monomers. A brand of copolymer of ethylene and vinyl alcohol distributed commercially under the trade name EVAL by Aldrich Chemical Co. of Milwaukee, Wis., and manufactured by EVAL Company of America of Lisle, Ill., can be used.

Other suitable polymers can also be used for making a drug-polymer layer, the optional primer layer, the topcoat layer and the finishing coat layer. Representative examples include poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoesters, polyanhydride, poly(glycolic acid), poly(D,L-lactic acid), poly(glycolic acid-co-trimethylene carbonate), polyphosphoesters, polyphosphoester urethanes, poly(amino acids), cyanoacrylates, poly(trimethylene carbonate), poly(iminocarbonate), co-poly(ether-esters) (e.g. PEO/PLA), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinylidene halides (such as polyvinylidene fluoride and polyvinylidene chloride), polyvinyl ethers (such as polyvinyl methyl ether), polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as NYLON 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellulose nitrate, cellulose propionate, cellulose ethers, carboxymethyl cellulose, CELLOPHANE and mixtures thereof.

Poly(ethylene glycol) (PEG) is one example of a polymer that can be included in the topcoat layer and/or the finishing coat layer. PEG is a biologically compatible product having the formula H—[O—$CH_2$—$CH_2$—O—$CH_2$—$CH_2$]$_n$—OH, and can have a molecular weight within a range of between about 1,000 and about 100,000 Daltons, for example, between 2,000 and 10,000 Daltons, such as 5,000 Daltons. The value of the integer "n" in the formula of PEG is about 56 for PEG having molecular weight of about 5,000.

Other suitable polymers can also be used to form in the topcoat layer and/or the finishing coat layer. Representative examples include heparin, hyaluronic acid, and silk-elastin protein block-copolymer. Heparin comprises a mixture of sulfated polysaccharide chains based on D-glucosamine and D-glucoronic or L-iduronic acid. A brand of heparin known under the trade name DURAFLO can be used. DURAFLO can be obtained from Baxter Healthcare Corporation of Deerfield, Ill. Hyaluronic acid is a linear polysaccharide composed of disaccharide units of N-acetylglucosamine and D-glucoronic acid. In hyaluronic acid, uronic acid and the aminosugar are linked by alternating $\beta$-1,4 and $\beta$-1,3 glucosidic bonds. Silk-elastin protein block-copolymers combine the repeating blocks of amino acids thus providing the copolymer with the mechanical strength characterizing silk and the flexibility characterizing elastin. Silk-elastin block-copolymer can be obtained from Protein Polymer Technologies, Inc. of San Diego, Calif. According to an embodiment of the present invention, the stent coating can comprise interpenetrating polymer networks (IPN). For the purposes of the present invention, a definition of the IPN used by the International Union of Pure and Applied Chemistry (TUPAC) is adopted. In other words, an IPN structure represents two or more polymer networks that are physically entangled. One example of an IPN that can be used is a surface hydrogel.

One example of a product that can be used for forming the IPN is a PEG-based unsaturated product, for example, prepolymer of PEG-acrylate or methacrylate having a general formula $CH_2$=CX—COO—[$CH_2$—$CH_2$—O]$_n$—H, where X is hydrogen (acrylates) or methyl (methacrylates). Weight average molecular weight of PEG-acrylate or methacrylate can be within a range of about 10,000 to 100,00 Daltons. PEG-acrylate prepolymer can be applied on the surface of the drug-polymer or topcoat layer and cured, for example, using a radical initiator which is activated by UV radiation (UV initiators), light (light initiators), or heat (thermal initiators). Examples of appropriate initiators include acetophenone, 2,2-dimethoxy-2-phenol-acetophenone (UV initiators), camproquinone, ethyl-4-N,N,-dimethyl aminobenzoate (light initiators), and benzoyl peroxide (thermal initiator). As a result of the curing process, PEG-acrylate will partially cross-link and partially physically entangle with the polymer of the underlying layer thus forming the outermost coat layer which includes an IPN. PEG-acrylate or methacrylate is intended to broadly include poly(ethylene glycol)-diacrylate (PEG-diacrylate) and poly(ethylene glycol)-dimethacrylate (PEG-dimethacrylate). PEG-acrylate or methacrylate and PEG-diacrylate or dimethacrylate can be optionally terminated, for example, with stearic acid, to form PEG-acrylate-stearate PEG-methacrylate-stearate, respectively.

Examples of other products that can be used for forming the IPN include such unsaturated reactive products as N-vinylpyrrolidone, heparin and its derivatives, hyaluronic acid and its derivatives, some hydrogel-forming products such as poly(butyleneterephthalate-co ethylene glycol) (PBT-PEG), and mixtures of any of these products with each other or with PEG-acrylate or methacrylate.

Suitable derivatives of heparin include sodium heparin (Na-Hep), heparin benzalkonium chloride (HBAC), and heparin tridodecyl methyl ammonium chloride (HTDMAC). Derivatives of heparin can also include heparin modified by introduction of photoactivatable groups in the heparin molecule (the groups that are inactive under ambient conditions but become reactive when irradiated by UV-light, for example, at the frequency of about 360 nm). Examples of photoactiva table groups include groups derived from benzophenone or dithiocarbonate. Methods of introducing the photoactivatable groups into the molecules of heparin are known to those having ordinary skill in the art. Other derivatives of heparin can include heparin containing a moiety that tends to bind to albumin, for example a the $-(CH_2)_{18}-$ moiety.

The coatings of all the embodiments of the present invention have been described in conjunction with a stent. However, the coatings can also be used with a variety of other medical devices. Examples of the implantable medical device, that can be used in conjunction with the embodiments of this invention include stent-grafts, grafts (e.g., aortic grafts), artificial heart valves, cerebrospinal fluid shunts, pacemaker electrodes, coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention.

"MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

EXAMPLES

Embodiments of the present invention can be further illustrated by the following Examples.

Example 1

A first composition can be prepared by mixing the following components:

(a) between about 0.1 mass % and about 15 mass %, for example, about 2.0 mass % of EVAL;

(b) between about 0.05 mass % and about 1.0 mass %, for example, about 1.0 mass % of EVEROLIMUS; and (c) the balance, dimethylacetamide (DMAC) solvent.

The first composition can be applied onto the surface of a stent (with or without the primer layer) and dried, to form a drug-polymer layer, for example, by spraying. An EFD spray head can be used, having a 0.014 inch fan nozzle with a feed pressure of about 0.2 atm (3 psi) and an atomization pressure of between about 1 atm and 1.3 atm (15 to 20 psi). The total amount of solids of the drug-polymer layer can be about 300 micrograms (µg). "Solids" is defined as the amount of the dry residue deposited on the stent after all volatile organic compounds (e.g., the solvent) have been removed.

A second composition can be prepared by mixing the following components::

(d) between about 0.1 mass % and about 15 mass %, for example, about 2.0 mass % of EVAL; and (e) the balance of DMAC solvent.

The second composition can be applied onto the dried drug-polymer layer, for example, by spraying or dipping, to form the topcoat layer. The topcoat layer can have, for example, a total solids weight of about 250 µg.

A third composition can be prepared by mixing the following components:

(g) between about 0.1 mass % and about 15 mass %, for example, about 2.0 mass % of EVAL;

(h) between about 0.1 mass % and about 5 mass %, for example, about 1.0 mass % of DURAFLO;

(i) between about 25 mass % and about 30 mass %, for example, 27.85 mass % of dimethylsulfoxide (DMSO) solvent;

(j) between about 5 mass % and about 6 mass %, for example, 5.65 mass % of tethrahydrofurane (THF) solvent; and (k) the balance, DMAC solvent.

The third composition can be applied onto the dried topcoat layer, for example, by spraying or dipping, to form the finishing coat layer having a total solids weight of about 200 µg.

Example 2

A first composition can be prepared by mixing the following components:

(a) between about 0.1 mass % and about 15 mass %, for example, about 2.0 mass % of EVAL;

(b) between about 0.05 mass % and about 1.0 mass %, for example, about 0.7 mass % of EVEROLIMUS; and (c) the balance, DMAC solvent.

The first composition can be applied onto a stent as described in Example 1, for example, by spraying, to form a drug-polymer layer with about 100 µg of total solids.

A second composition can be prepared by mixing the following components:

(d) between about 0.1 mass % and about 15 mass %, for example, about 2 mass % of EVAL; and (e) the balance, DMAC solvent.

The second composition can be applied onto the dried drug-polymer layer, for example, by spraying, to form the topcoat layer having a total solids weight of about 300 µg.

A third composition can be prepared by mixing the following components:

(f) between about 0.1 mass % and about 15 mass %, for example, about 2.0 mass % of EVAL;

(g) between about 0.1 mass % and about 5 mass %, for example, about 1.0 mass % of poly(ethylene glycol) having molecular weight of about 5,000 Daltons (PEG5000); and (h) the balance, DMAC solvent.

The third composition can be applied onto the dried topcoat layer, for example, by spraying or dipping, to form the finishing coat layer having a total solids weight of about 200 µg.

Example 3

A first composition can be prepared by mixing the following components:
(a) between about 0.1 mass % and about 15 mass %, for example, about 2.0 mass % of EVAL;
(b) between about 0.05 mass % and about 1.0 mass %, for example, about 0.7 mass % of EVEROLIMUS; and
(c) the balance, DMAC solvent.

The first composition can be applied onto a stent as described in Example 1, for example, by spraying, to form a drug-polymer layer with about 200 µg of total solids.

A second composition can be prepared by mixing the following components:
(d) between about 0.1 mass % and about 15 mass %, for example, about 2 mass % of EVAL; and
(e) the balance, DMAC solvent.

The second composition can be applied onto the dried drug-polymer layer, for example, by spraying, to form the topcoat layer having a total solids weight of about 300 µg.

A third composition can be prepared by mixing the following components:
(f) between about 0.1 mass % and about 15 mass %, for example, about 1.3 mass % of EVAL;
(g) between about 0.1 mass % and about 5 mass %, for example, about 0.7 mass % of PEG5000; and
(h) the balance, DMAC solvent.

The third composition can be applied onto the dried topcoat layer, for example, by spraying or dipping, to form the finishing coat layer having a total solids weight of about 200 µg.

Example 4

A stent can be coated as described in Example 3, except the drug-polymer layer can have a total solids weight of about 400 µg, and the finishing coat layer can have a total solids weight of about 150 µg.

Example 5

A first composition can be prepared by mixing the following components:
(a) between about 0.1 mass % and about 15 mass %, for example, about 2.0 mass % of EVAL;
(b) between about 0.05 mass % and about 1.5 mass %, for example, about 1.2 mass % of EVEROLIMUS; and
(c) the balance, DMAC solvent.

The first composition is applied onto a stent as described in Example 1, for example, by spraying, to form a drug-polymer layer with about 420 µg of total solids.

A second composition can be prepared by mixing the following components:
(d) between about 0.1 mass % and about 15 mass %, for example, about 2 mass % of EVAL; and
(e) the balance, DMAC solvent.

The second composition can be applied onto the dried drug-polymer layer, for example, by spraying, to form the topcoat layer having a total solids weight of about 300 µg.

A third composition can be prepared by mixing the following components:
(f) between about 0.1 mass % and about 15 mass %, for example, about 1.3 mass % of EVAL;
(g) between about 0.1 mass % and about 5 mass %, for example, about 0.7 mass % of PEG5000; and
(h) the balance, DMAC solvent.

The third composition can be applied onto the dried topcoat layer, for example, by spraying or dipping, to form the finishing coat layer having a total solids weight of about 150 µg.

Example 6

A first composition can be prepared by mixing the following components:
(a) between about 0.1 mass % and about 15 mass %, for example, about 1.4 mass % of EVAL;
(b) between about 0.05 mass % and about 1.5 mass %, for example, about 0.7 mass % of the drug β-estradiol; and
(c) the balance, DMAC solvent.

The first composition can be applied onto a stent as described in Example 1, for example, by spraying, to form a drug-polymer layer with about 450 µg of total solids.

A second composition can be prepared by mixing the following components:
(d) between about 0.1 mass % and about 15 mass %, for example, about 2 mass % of EVAL; and
(e) the balance, DMAC solvent.

The second composition can be applied onto the dried drug-polymer layer, for example, by spraying, to form the topcoat layer having a total solids weight of about 250 µg.

A third composition can be prepared by mixing the following components:
(f) between about 0.1 mass % and about 15 mass %, for example, about 1.3 mass % of EVAL;
(g) between about 0.1 mass % and about 5 mass %, for example, about 0.7 mass % of PEG5000; and
(h) the balance, DMAC solvent.

The third composition can be applied onto the dried topcoat layer, for example, by spraying or dipping, to form the finishing coat layer having a total solids weight of about 150 µg.

Example 7

A first composition can be prepared by mixing the following components:
(a) between about 0.1 mass % and about 15 mass %, for example, about 1.0 mass % of EVAL;
(b) between about 0.05 mass % and about 1.5 mass %, for example, about 1.0 mass % of β-estradiol; and
(c) the balance, DMAC solvent.

The first composition can be applied onto a stent as described in Example 1, for example, by spraying, to form a drug-polymer layer with about 320 µg of total solids.

A second composition can be prepared by mixing the following components:
(d) between about 0.1 mass % and about 15 mass %, for example, about 2 mass % of EVAL; and
(e) the balance, DMAC solvent.

The second composition can be applied onto the dried drug-polymer layer, for example, by spraying, to form the topcoat layer having a total solids weight of about 250 µg.

A third composition can be prepared by mixing the following components:
(f) between about 0.1 mass % and about 15 mass %, for example, about 1.3 mass % of EVAL;
(g) between about 0.1 mass % and about 5 mass %, for example, about 0.7 mass % of PEG5000; and
(h) the balance, DMAC solvent.

The third composition can be applied onto the dried topcoat layer, for example, by spraying or dipping, to form the finishing coat layer having a total solids weight of about 150 µg.

Example 8

A first composition can be prepared by mixing the following components:
(a) between about 0.1 mass % and about 15 mass %, for example, about 1.0 mass % of EVAL;
(b) between about 0.05 mass % and about 1.5 mass %, for example, about 1.0 mass % of β-estradiol; and
(c) the balance, DMAC solvent.

The first composition can be applied onto a stent as described in Example 1, for example, by spraying, to form a drug-polymer layer with about 200 µg of total solids.

A second composition can be prepared by mixing the following components:
(d) between about 0.1 mass % and about 15 mass %, for example, about 2 mass % of EVAL; and
(e) the balance, DMAC solvent.

The second composition can be applied onto the dried drug-polymer layer, for example, by spraying, to form the topcoat layer having a total solids weight of about 200 µg.

A third composition can be prepared by mixing the following components:
(f) between about 0.1 mass % and about 15 mass %, for example, about 0.5 mass % of EVAL;
(g) between about 0.1 mass % and about 5 mass %, for example, about 0.25 mass % of hyaluronic acid; and
(h) the balance, DMSO solvent.

The third composition can be applied onto the dried topcoat layer, for example, by centrifugation, to form the finishing coat layer having a total solids weight of about 150 µg. The method of coating by centrifugation is known to those having ordinary skill in the art.

Example 9

A stent can be coated as described in Example 8, except the drug-polymer and the topcoat layer each can have a total solids weight of about 100 µg.

Example 10

A first composition can be prepared by mixing the following components:
(a) between about 0.1 mass % and about 15 mass %, for example, about 1.3 mass % of EVAL;
(b) between about 0.05 mass % and about 1.5 mass %, for example, about 0.7 mass % of β-estradiol; and
(c) the balance, DMAC solvent.

The first composition can be applied onto a stent as described in Example 1, for example, by spraying, to form a drug-polymer layer with about 200 µg of total solids.

A second composition can be prepared by mixing the following components:
(d) between about 0.1 mass % and about 15 mass %, for example, about 2 mass % of EVAL; and
(e) the balance, DMAC solvent.

The second composition can be applied onto the dried drug-polymer layer, for example, by spraying, to form the topcoat layer having a total solids weight of about 200 µg.

A third composition can be prepared by mixing the following components:
(f) between about 0.1 mass % and about 15 mass %, for example, about 0.5 mass % of EVAL;
(g) between about 0.1 mass % and about 5 mass %, for example, about 0.25 mass % of hyaluronic acid; and
(h) the balance, DMSO solvent.

The third composition can be applied onto the dried topcoat layer, for example, by centrifugation, to form the finishing coat layer having a total solids weight of about 150 µg.

Example 11

A first composition can be prepared by mixing the following components:
(a) between about 0.1 mass % and about 15 mass %, for example, about 1.0 mass % of EVAL;
(b) between about 0.05 mass % and about 1.5 mass %, for example, about 1.0 mass % of β-estradiol; and
(c) the balance, DMAC solvent.

The first composition can be applied onto a stent as described in Example 1, for example, by spraying, to form a drug-polymer layer with about 200 µg of total solids.

A second composition can be prepared by mixing the following components:
(d) between about 0.1 mass % and about 15 mass %, for example, about 2 mass % of EVAL; and
(e) the balance, DMAC solvent.

The second composition can be applied onto the dried drug-polymer layer, for example, by spraying, to form the topcoat layer having a total solids weight of about 200 µg.

A third composition can be prepared by mixing the following components:
(f) between about 0.1 mass % and about 15 mass %, for example, about 0.5 mass % of silk elastin product;
(g) between about 0.1 mass % and about 5 mass %, for example, about 0.5 mass % of hyaluronic acid; and
(h) the balance, distilled water.

The third composition can be applied onto the dried topcoat layer, for example, by centrifugation, to form the finishing coat layer having a total solids weight of about 150 µg.

Example 12

A stent can be coated as described in Example 11, except the drug-polymer and the topcoat layer each can have a total solids weight of about 100 µg.

Example 13

A first composition can be prepared by mixing the following components:
(a) between about 0.1 mass % and about 15 mass %, for example, about 1.3 mass % of EVAL;
(b) between about 0.05 mass % and about 1.5 mass %, for example, about 0.7 mass % of β-estradiol; and
(c) the balance, DMAC solvent.

The first composition can be applied onto a stent as described in Example 1, for example, by spraying, to form a drug-polymer layer with about 200 µg of total solids.

A second composition can be prepared by mixing the following components:
(d) between about 0.1 mass % and about 15 mass %, for example, about 2 mass % of EVAL; and
(e) the balance, DMAC solvent.

The second composition can be applied onto the dried drug-polymer layer, for example, by spraying, to form the topcoat layer having a total solids weight of about 200 µg.

A third composition can be prepared by mixing the following components:

(f) between about 0.1 mass % and about 15 mass %, for example, about 0.5 mass % of silk elastin product;
(g) between about 0.1 mass % and about 5 mass %, for example, about 0.5 mass % of hyaluronic acid; and
(h) the balance, distilled water.

The third composition can be applied onto the dried topcoat layer, for example, by centrifugation, to form the finishing coat layer having a total solids weight of about 150 µg.

Examples 1-13 are summarized in Table 1.

TABLE 1

A Summary of the Formulations of Examples 1-13

| | Drug-Polymer Layer | | | Topcoat Layer | | Finishing Coat Layer | |
|---|---|---|---|---|---|---|---|
| Example | Polymer, % | Drug, % | Weight of the layer, µg | Polymer, % | Weight of the layer, µg | Polymer, % | Weight of the layer, µg |
| 1 | EVAL, 2 | EVEROLIMUS, 1 | 300 | EVAL, 2 | 250 | EVAL, 2 DFLO, 1 | 200 |
| 2 | EVAL, 2 | EVEROLIMUS, 0.7 | 100 | EVAL, 2 | 300 | EVAL, 2 PEG500, 1 | 200 |
| 3 | EVAL, 2 | EVEROLIMUS, 0.7 | 20 | EVAL, 2 | 300 | EVAL, 1.3 PEG5000, 0.7 | 200 |
| 4 | EVAL, 2 | EVEROLIMUS, 0.7 | 400 | EVAL, 2 | 300 | EVAL, 1.3 PEG5000, 0.7 | 150 |
| 5 | EVAL, 2 | EVEROLIMUS, 1.2 | 420 | EVAL, 2 | 300 | EVAL, 1.3 PEG5000, 0.7 | 150 |
| 6 | EVAL, 1.4 | Estradiol, 0.7 | 450 | EVAL, 2 | 250 | EVAL, 1.3 PEG5000, 0.7 | 150 |
| 7 | EVAL, 1 | Estradiol, 1 | 320 | EVAL, 2 | 250 | EVAL, 1.3 PEG5000, 0.7 | 150 |
| 8 | EVAL, 1 | Estradiol, 1 | 200 | EVAL, 2 | 200 | EVAL, 0.5 Hyaluronic acid, 0.25 | 150 |
| 9 | EVAL, 1 | Estradiol, 1 | 100 | EVAL, 2 | 100 | EVAL, 0.5 Hyaluronic acid, 0.25 | 150 |
| 10 | EVAL, 1.3 | Estradiol, 0.7 | 150 | EVAL, 2 | 150 | EVAL, 0.5 Hyaluronic acid, 0.25 | 150 |
| 11 | EVAL, 1 | Estradiol, 1 | 200 | EVAL, 2 | 200 | Silk Elastin, 0.5 Hyaluronic acid, 0.5 | 150 |
| 12 | EVAL, 1 | Estradiol, 1 | 100 | EVAL, 2 | 100 | Silk Elastin, 0.5 Hyaluronic acid, 0.5 | 150 |
| 13 | EVAL, 1.3 | Estradiol, 0.7 | 200 | EVAL, 0.5 | 200 | Silk Elastin, 0.5 Hyaluronic acid, 0.5 | 150 |

Example 14

A drug-polymer layer can be formed on a stent as described in Example 1. A composition can be prepared, the composition including:

(a) about 3 mass % of PEG-acrylate having $M_w$ within a range of about 10,000 and 100,000;
(b) about 1 mass % of 2,2-dimethoxy-2-phenol-acetophenone; and
(c) the balance a solvent mixture, the mixture containing de-ionized water and ethanol in a mass ratio of about 4:1.

The composition can be applied on the dried drug-polymer layer and irradiated with UV-light at a wavelength of 360 nm for about 10 seconds, followed by drying, to form a topcoat layer comprising an IPN based on poly(PEG-acrylate).

Example 15

The stent can be coated as described in Example 14, except that the same amount of benzoyl peroxide can be used the instead of acetophenone. The topcoat layer-forming IPN can be formed by subjecting the stent to a temperature of about 80° C. for about 5 minutes.

Example 16

A drug-polymer layer can be formed on a stent as described in Example 1. A composition can be prepared, the composition including:

(a) about 20 mass % of N-vinylpyrrolidone;
(b) about 3 mass % of PEG-acrylate having $M_w$ within a range of about 10,000 and 100,000;
(c) about 1 mass % of 2,2-dimethoxy-2-phenol-acetophenone; and
(d) the balance of a solvent mixture, the mixture containing de-ionized water and ethanol in a mass ratio of about 4:1.

The composition can be applied on a stent and a topcoat layer comprising an IPN can be formed as described in Example 14.

Example 17

A drug-polymer layer can be formed on a stent as described in Example 1. A composition can be prepared, the composition including:

(a) about 3 mass % of PEG-acrylate having $M_w$ within a range of about 10,000 and 100,000;
(b) about 3 mass % of heparin benzalkonium chloride (HBAC);
(c) about 1 mass % of acetophenone; and
(d) the balance a solvent mixture, the mixture containing iso-propanol and dimethylacetamide in a mass ratio of about 14:1.

The composition can be applied on a stent and a topcoat layer comprising an IPN can be formed as described in Example 14.

Example 18

A drug-polymer layer can be formed on a stent as described in Example 1. A composition can be prepared, the composition including:

(a) about 2 mass % of EVAL;
(b) about 0.7 mass % of PEG having $M_w$ of about 17,500 Daltons;
(c) about 0.7 mass % of PEG-diacrylate having $M_w$ of about 10,000 Daltons;
(d) about 0.7 mass % of HBAC;
(e) about 0.1 mass % of 2,2-dimethoxy-2-phenol-acetophenone; and
(f) the balance dimethylacetamide solvent.

The composition can be applied on a stent and a topcoat layer comprising an IPN can be formed as described in Example 14.

Example 19

A drug-polymer layer can be formed on a stent as described in Example 1. A composition can be prepared, the composition including:

(a) about 7 mass % of EVAL;
(b) about 2 mass % of PEG having $M_w$ of about 17,500 Daltons;
(c) about 2 mass % of PEG-diacrylate having $M_w$ of about 10,000 Daltons;
(d) about 2 mass % of HBAC;
(e) about 0.5 mass % of 2,2-dimethoxy-2-phenol-acetophenone; and
(f) the balance dimethylacetamide solvent.

The composition can be applied on a stent by spin coating and a topcoat layer comprising an IPN can be formed.

Example 20

A drug-polymer layer can be formed on a stent as described in Example 1. A composition can be prepared, the composition including:

(a) about 2 mass % of EVAL;
(b) about 0.4 mass % of PEG having $M_w$ of about 17,500 Daltons;
(c) about 0.2 mass % of HBAC; and
(d) the balance of dimethylacetamide solvent.

The composition can be applied on a stent, for example, by spraying, to form a topcoat layer.

Example 21

A drug-polymer layer can be formed on a stent as described in Example 1. A composition can be prepared, the composition including:

(a) about 3 mass % of EVAL;
(b) about 2 mass % of PEG having $M_w$ of about 17,500 Daltons;
(c) about 2 mass % of sodium heparin (Na-Hep); and
(d) the balance, a solvent blend, the blend comprising formamide (FA), methanol (MeOH) and dimethylacetamide (DMAC) in a mass ratio FA:MeOH:DMAC of about 1:1.05:3.

To prepare the composition, Na-Hep can be dissolved in FA first at a temperature between about 60° C. and 100° C., to form about 10% Na-Hep/FA solution, followed by adding EVAL, PEG, MeOH and DMAC to the Na-Hep/FA solution.

The composition can be applied on a stent, for example, by spraying while the temperature of the composition is maintained between about 55° C. and 70° C., to form a topcoat layer.

Example 22

A first composition can be prepared, the composition including:

(a) about 2 mass % of PBT-PEG having the formula (I):

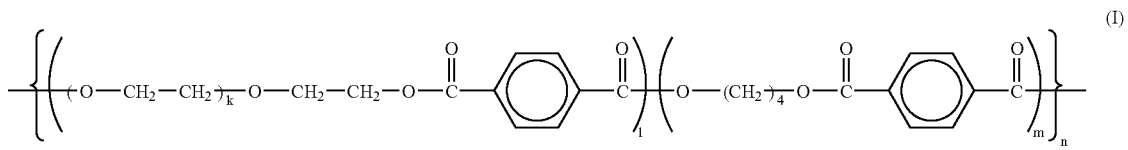

wherein k is about 90 (corresponding to number averaged molecular weight of the PEG fragment of about 4,000), the PBT-PEG polymer comprises about 80% units derived from PEG and about 20% units derived from butylene terephthalate;

(b) the balance, a solvent blend, the blend comprising trichloroethane and chloroform in a mass ratio between trichloroethane and chloroform of about 4:1.

The first composition can be applied onto the surface of a stent, for example, by spraying, and dried at about 140° C. for about 1 hour, to form a primer layer. An EFD spray head can be used, having a 0.014 fan nozzle with a feed pressure of about 0.2 atm (3 psi) and an atomization pressure of between about 1 atm and 1.3 atm (15 to 20 psi). The total amount of solids of the primer layer can be about 100 μg.

A second composition can be prepared, the composition including:

(a) about 2 mass % of PBT-PEG described above;
(b) about 1 mass % of EVEROLIMNS; and
(c) the balance, a solvent blend, the blend comprising trichloroethane and chloroform in a mass ratio between trichloroethane and chloroform of about 4:1.

The second composition can be applied onto the dried primer layer, for example, by spraying, and dried at about 50° C. for about 2 hours, to form a drug-polymer layer. The total amount of solids of the drug-polymer layer can be about 300 μg.

A third composition can be prepared, the composition including:

(a) about 2 mass % of PBT-PEG described by the formula (I), wherein K is about 90, the PBT-PEG polymer comprises about 80% of units derived from PEG and about 20% of units derived from butylene terephthalate, and wherein $T_m$ of the PEG fragment is about 47° C., and $T_m$ of the butylene terephthalate fragment is about 173° C.

(b) the balance, a 1,4-dioxane solvent blend.

The third composition can be applied onto the dry drug-polymer layer, for example, by spraying, and dried at about 50° C. for about 1 hour, to form a topcoat layer. The total amount of solids of the topcoat layer can be about 100 μg.

Examples 14-22 are summarized in Table 2.

TABLE 2

A Summary of the Formulations of Examples 14-22

| | Drug-Polymer Layer | | | Topcoat Layer | |
|---|---|---|---|---|---|
| Example | Polymer, % | Drug, % | Weight of the layer, μg | Products-Precursors for IPN | Amount, % |
| 14/15 | EVAL, 2 | EVEROLIMUS, 1 | 300 | PEG-Acrylate | 3 |
| 16 | EVAL, 2 | EVEROLIMUS, 1 | 300 | N-vinylpyrrolidone | 20 |
| | | | | PEG-Acrylate | 3 |
| 17 | EVAL, 2 | EVEROLIMUS, 1 | 300 | Heparin Benzalkonium Chloride | 3 |
| | | | | PEG-Acrylate | 3 |
| 18 | EVAL, 2 | EVEROLIMUS, 1 | 300 | EVAL | 2 |
| | | | | Heparin Benzalkonium Chloride | 0.7 |
| | | | | PEG-Diacrylate | 0.7 |
| | | | | PEG | 0.7 |
| 19 | EVAL, 2 | EVEROLIMUS, 1 | 300 | EVAL | 7 |
| | | | | Heparin Benzalkonium Chloride | 2 |
| | | | | PEG-Diacrylate | 2 |
| | | | | PEG | 2 |
| 20 | EVAL, 2 | EVEROLIMUS, 1 | 300 | EVAL | 2 |
| | | | | PEG | 0.4 |
| | | | | Heparin Benzalkonium Chloride | 0.2 |
| 21 | EVAL, 2 | EVEROLIMUS, 1 | 300 | EVAL | 3 |
| | | | | PEG | 2 |
| | | | | Sodium Heparin | 2 |
| 22*⁾ | PBT-PEG, 2 | EVEROLIMUS, 1 | 300 | PBT-PEG | 2 |

*⁾The coating also has a PBT-PEG based primer layer.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for fabricating a coating on an implantable medical device, the method comprising:
    (a) forming a polymer layer on the device;
    (b) applying on the polymer layer a precursor of an interpenetrating polymer network; and
    (c) subjecting the device to a treatment to cause the precursor to form the interpenetrating polymer network on the device,
    wherein the precursor is selected from the group consisting of poly(ethylene glycol)-acrylate, poly(ethylene glycol)-diacrylate, N-vinylpyrrolidone, derivatives of heparin, hyaluronic acid, derivatives of hyaluronic acid, poly(butyleneterephthalate-co ethylene glycol) (PBT-PEG), and mixtures thereof, and
    wherein the derivative of heparin comprise heparin containing photoactivatable group(s), or heparin containing albumin-binding moiety(ies).

2. The method of claim 1, wherein the medical device is a stent.

3. The method of claim 1, wherein forming the polymer layer comprises including a therapeutic substance in the polymer layer.

4. The method of claim 3, wherein the therapeutic substance is selected from the group consisting of paclitaxel, docetaxel, rapamycin, 40-O-(2-hydroxy)ethyl-rapamycin, 40-O-(3-hydroxy)propyl-rapamycin, 40-O-[2-(2-hydroxy)ethoxy]ethyl-rapamycin, 40-O-tetrazole-rapamycin, and estradiol.

5. The method of claim 1, wherein the photoactivatable groups are derived from benzophenone or dithiocarbonate.

6. The method of claim 1, wherein the treatment includes exposing the device to UV-radiation.

7. The method of claim 6, further including adding a UV initiator to the precursor.

8. The method of claim 7, wherein the initiator comprises acetophenone or 2,2-dimethoxy-2-phenol-acetophenone.

9. The method of claim 1, wherein treatment includes exposing the device to light or to heat.

10. A method of fabricating a coating for a medical device comprising forming a coating including an interpenetrating polymer network and a drug on the medical device,
    wherein the coating includes a first layer and a second layer over the first layer,
    wherein the first layer comprises the drug and the second layer comprises the interpenetrating polymer network,
    wherein the interpenetrating polymer network is formed by applying on the medical device a precursor of the interpenetrating polymer network and subjecting the device to a treatment to cause the precursor to form the interpenetrating polymer network on the device, wherein the precursor is selected from the group consisting of poly(ethylene glycol)-acrylate, poly(ethylene glycol)-diacrylate, N-vinylpyrrolidone, derivatives of heparin, hyaluronic acid, derivatives of hyaluronic acid, poly(butyleneterephthalate-co ethylene glycol) (PBT-PEG), and mixtures thereof, and wherein the derivative of heparin comprise heparin containing photoactivatable group(s), or heparin containing albumin-binding moiety(ies).

11. The method of claim 10, wherein the photoactivatable groups are derived from benzophenone or dithiocarbonate.

12. The method of claim 10, wherein treatment includes exposing the device to UV-radiation.

13. The method of claim 12, further including adding a UV initiator to the precursor.

14. The method of claim 13, wherein the initiator comprises acetophenone or 2,2-dimethoxy-2-phenol-acetophenone.

15. The method of claim 10, wherein treatment includes exposing the device to light or to heat.

* * * * *